(12) United States Patent
Petersen

(10) Patent No.: US 6,457,369 B1
(45) Date of Patent: Oct. 1, 2002

(54) LOADING ASSEMBLY HAVING A SOFT ACTUATOR

(75) Inventor: Niel R. Petersen, Minnetonka, MN (US)

(73) Assignee: MTS Systems Corporation, Eden Prairie, MN (US)

( * ) Notice: Subject to any disclaimer, the term of this patent is extended or adjusted under 35 U.S.C. 154(b) by 0 days.

(21) Appl. No.: 09/438,010

(22) Filed: Nov. 10, 1999

Related U.S. Application Data
(60) Provisional application No. 60/108,372, filed on Nov. 13, 1998.

(51) Int. Cl.[7] ................................................. G01N 3/00
(52) U.S. Cl. ....................................................... 73/798
(58) Field of Search .......................... 73/816, 825, 840, 73/798

(56) References Cited

U.S. PATENT DOCUMENTS

| | | | |
|---|---|---|---|
| 2,750,795 A | 6/1956 | Federn | 73/92 |
| 2,773,482 A | 12/1956 | Dickie | 121/20 |
| 2,931,218 A | 4/1960 | Ottestad | 73/12 |
| 3,575,045 A | 4/1971 | Knights | 73/92 |
| 3,600,940 A * | 8/1971 | Schlegel | 73/816 |
| 3,909,776 A | 9/1975 | Broding et al. | 340/17 |
| 3,965,729 A * | 6/1976 | King, Jr. | 73/816 |
| 4,018,080 A | 4/1977 | Fletcher et al. | 73/15.6 |
| 4,056,974 A * | 11/1977 | Klinger et al. | 73/797 |
| 4,396,088 A | 8/1983 | Bayhi | 181/120 |
| 4,483,411 A | 11/1984 | Mifsud | 181/120 |
| 4,671,379 A | 6/1987 | Kennedy et al. | 181/106 |
| 4,679,441 A | 7/1987 | Johnson et al. | 73/798 |
| 4,834,210 A | 5/1989 | Kennedy | 181/106 |
| 4,850,449 A | 7/1989 | Cheung | 181/101 |
| 4,993,001 A | 2/1991 | Winbow et al. | 367/144 |
| 5,325,700 A | 7/1994 | Litten | 73/11.06 |
| 5,371,330 A | 12/1994 | Winbow | 181/106 |
| 5,491,306 A | 2/1996 | Gram | 181/106 |
| 5,540,099 A | 7/1996 | Harashima | 73/699 |

FOREIGN PATENT DOCUMENTS

| | | |
|---|---|---|
| EP | 0 479 399 A2 | 4/1992 |
| JP | 10153623 A | 11/1996 |

* cited by examiner

*Primary Examiner*—Max Noori
(74) *Attorney, Agent, or Firm*—Westman, Champlin & Kelly, P.A.; S. Koehler

(57) ABSTRACT

A loading assembly for applying a load to a test specimen includes a container having a volume of compressible fluid for providing a spring. A cylinder having a bore operably connected to the container. A piston is slidable in the bore and is operably coupleable to the test specimen. A valve fluidly coupled to the bore selectively provides fluid to the bore to displace the piston. A controller controls the valve to cause nonresonant displacement of the piston.

21 Claims, 5 Drawing Sheets

US 6,457,369 B1

LOADING ASSEMBLY HAVING A SOFT ACTUATOR

CROSS-REFERENCE TO RELATED APPLICATION

This application is based on and claims priority of Provisional Patent Application 60/108,372, filed Nov. 13, 1998, which is also hereby incorporated by reference in its entirety.

BACKGROUND OF THE INVENTION

The present invention relates to loading assemblies used for applying selected loads to test specimens. More particularly, the present invention relates to a loading assembly capable of applying high loads, yet compliant for disturbing input motions.

A loading assembly generally includes an actuator and connecting elements to connect the actuator to the test specimen in order to apply a selected force or moment thereto. When hydraulic actuators are used, substantial loads can be applied. For instance, loading assemblies are generally known and used for simulating loads experienced by cars, trucks, motorcycles, planes, etc, or parts therefor. In the case of cars, trucks and motorcycles, the loading assembly can be used to simulate loads applied to the vehicle as the vehicle traverses a road or other course.

Although the loading assemblies mentioned above can apply high loads to simulate forces and moments applied to a test specimen such as a motor vehicle, there exists other loads which as of yet have not been properly simulated. For instance, racecars include air foils that are designed to generate substantial downwardly directed forces in order to help the racecar maintain contact with the road. However, in the presence of this downwardly directed force, the racecar may experience rapid chassis disturbances for example from aerodynamic blanking from another car in front, changes in the racecar pitch due to braking and centrifugal accelerations due to cornering at the friction limits of the tires. Although hydraulic actuators are well suited for applying a load that simulates the magnitude of the downforce exerted upon the racecar, the actuator is too stiff in the presence of these displacement disturbances. In other words, for higher frequency (e.g. greater than 2 Hertz) input velocity disturbances or displacements of the vehicle, the actuator and connecting components generally act as a rigid connection.

Although it has been known to mechanically soften an actuator by using a coiled spring connected in series with the actuator and a test specimen, or using a bending beam assembly, these techniques are generally unsatisfactory. In many instances, a long stroke actuator is needed in order to compress the coiled spring to generate the desired spring rate. This limits the effective operating range of the loading assembly. In addition, significant changes in the spring rate may require replacement of the mechanical spring. The spring must also be fully deflected in order to apply full load.

Accordingly, there is a need for an improved loading assembly that can apply substantial loads to a test specimen, yet be compliant for high frequency input disturbances.

SUMMARY OF THE INVENTION

A loading assembly for applying a load to a test specimen includes a container having a volume of compressible fluid for providing a spring. A cylinder having a bore operably connected to the container. A piston is slidable in the bore and is operably coupleable to the test specimen. A flow control valve fluidly coupled to the bore selectively provides fluid to the bore to displace the piston. A controller controls the valve to cause non-resonant displacement of the piston.

In one embodiment, the container comprises an accumulator having a volume of compressible gas. In another embodiment, the volume of compressible liquid in the container is equal to or greater than a maximum volume of a chamber defined by displacement of the piston in the bore.

DETAILED DESCRIPTION OF THE ILLUSTRATIVE EMBODIMENTS

Figure 1:
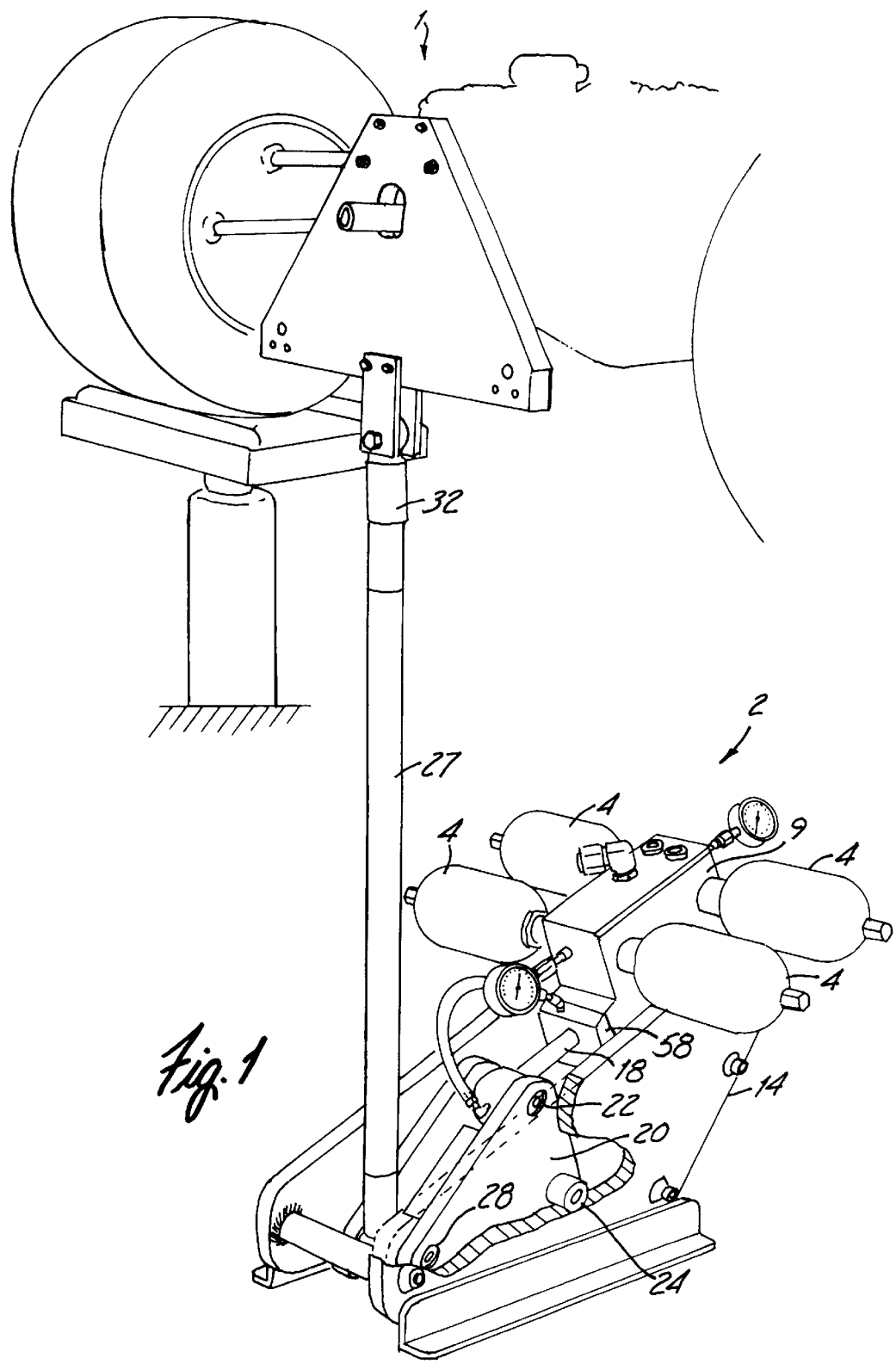
FIG. 1 is a schematic diagram of a loading assembly of the present invention.
Figure 2:
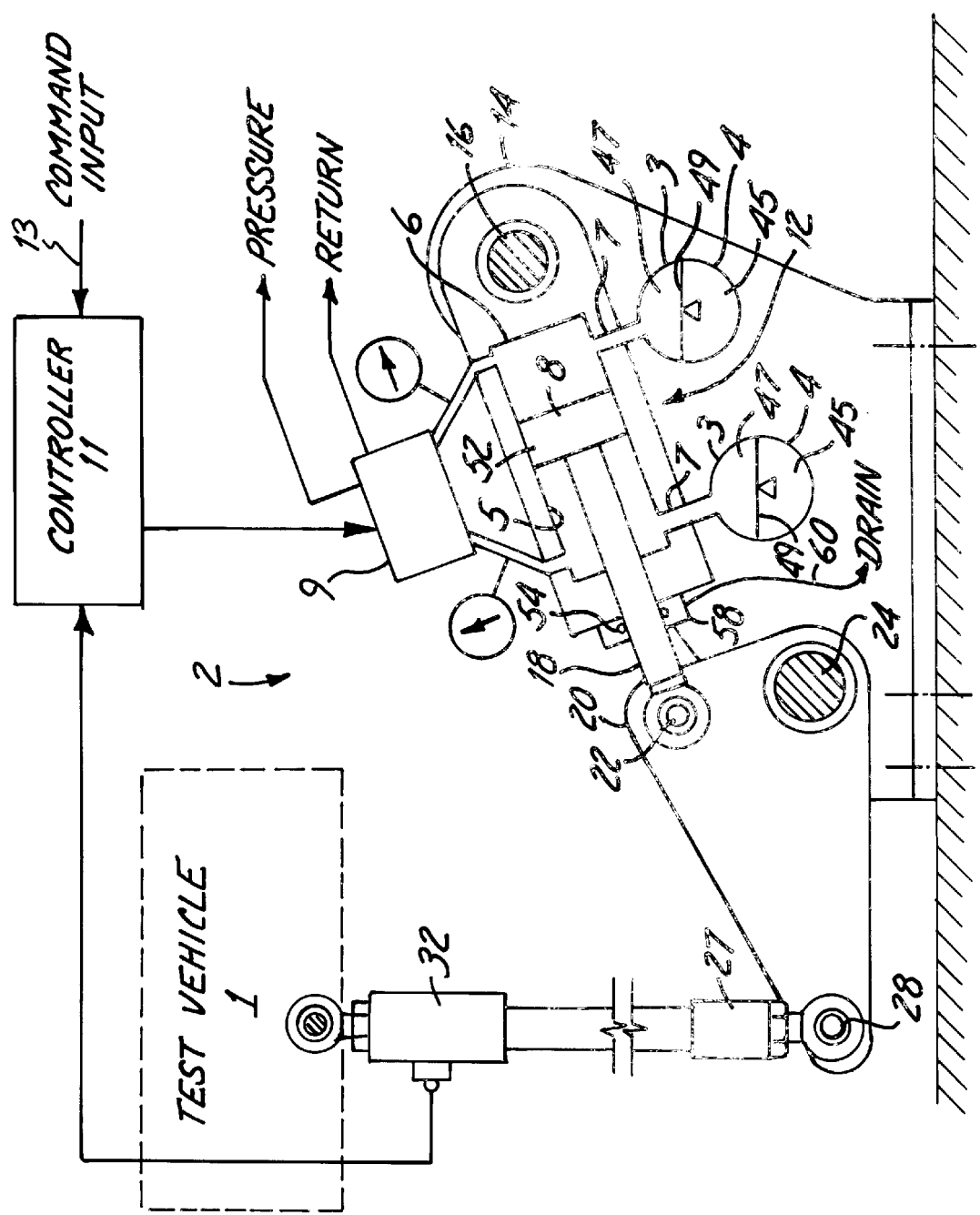
FIG. 2 is a perspective view of the loading assembly.
Figure 3:
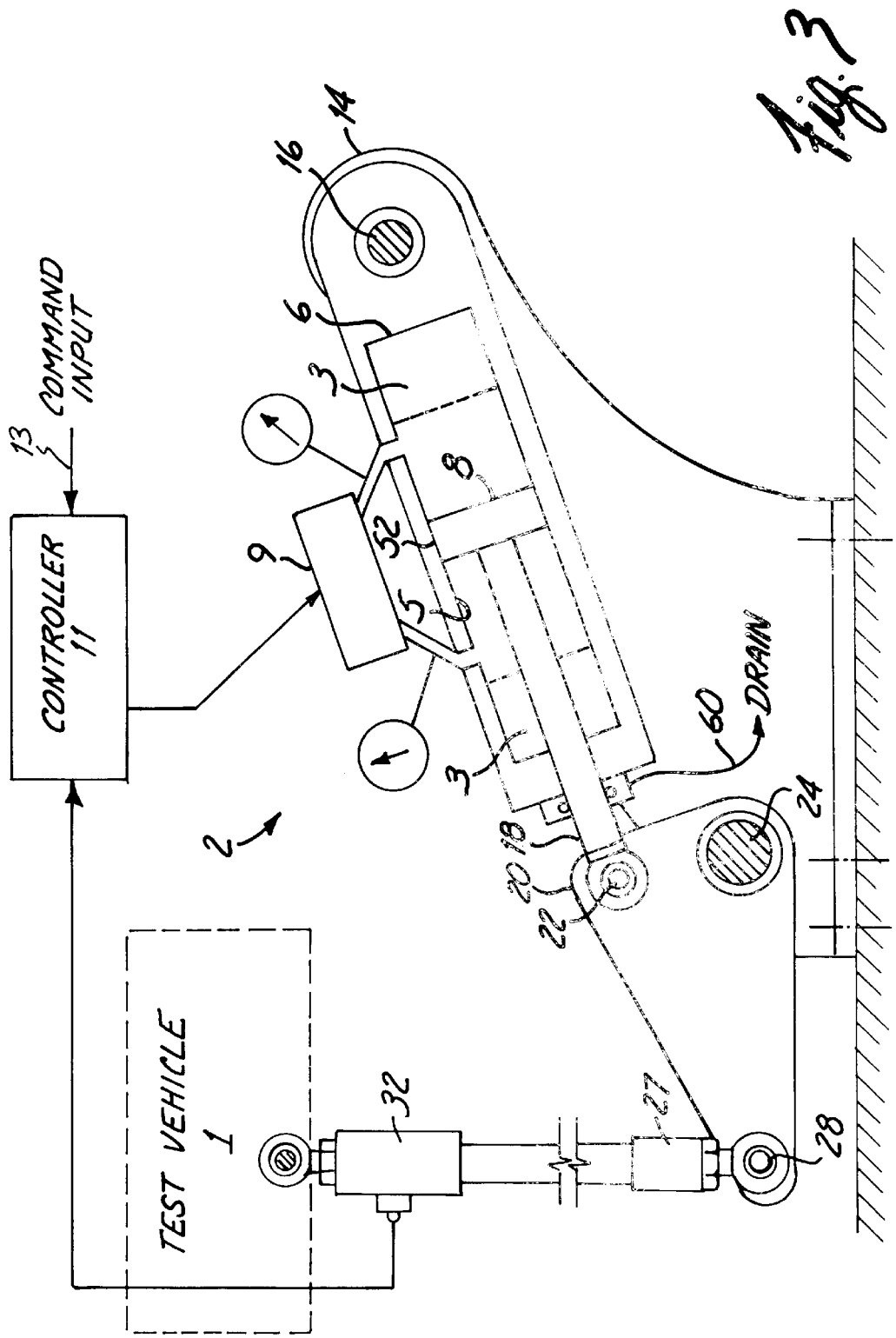
FIG. 3 is a schematic diagram of a second embodiment of a loading assembly.

The present invention relates to actuator assemblies for applying or simulating loads on a test specimen. A particularly useful application of the present invention is to simulate downforces on a racecar 1. Referring to FIGS. 1 and 2, a loading assembly 2 for applying a load to a test specimen 1 (herein a racecar) includes a volume of compressible fluid 3 for providing a spring. In the embodiment illustrated, the volume of compressible fluid 3 is disposed within a container 4 that is fluidly coupled to a bore 5 of a cylinder 6 through a port 7. However, as appreciated by those skilled in the art, the volume of compressible fluid 3 can be disposed in the cylinder 5 on an end thereof, which a piston 8 does not reach. FIG. 3 schematically illustrates this embodiment.

The piston 8 is slidable in the bore 5 and is operably coupleable to the test specimen 1. The piston 8 and the bore 5 operate as a hydraulic actuator. A flow control valve 9 fluidly coupled to the bore 5 selectively provides hydraulic fluid to the bore 5 to displace the piston 8. A controller 11 receives a command input 13 and controls the valve 9 to cause nonresonant displacement of the piston 8 in the bore 5 in accordance with the command input 13. The loading assembly 2 can apply significant forces or moments to the test specimen 1, such as the downforce experienced by a racecar herein illustrated. However, as equally important, the loading assembly 2 is compliant to velocity or displacement disturbances of the test specimen 1 wherein the volume of compressible fluid 3 acts as a spring. Generally, hydraulic actuators as used in loading assemblies of the prior art minimize the amount of excess fluid in the bore 5 (portions of the bore 5 that the piston 8 does not reach) in order to reduce the weight of the actuator. Inclusion of additional fluid to act as a spring was not appreciated. Although gas springs have been used in resonant vibration systems, such as disclosed in U.S. Pat. No. 5,491,306, use of a volume of compressible fluid 3 in a nonresonant loading assembly 2 that generally applies static or non-oscillating loads is not known.

Referring back to FIG. 2, in one embodiment, the loading assembly 2 comprises a single-ended, double-acting servo hydraulic actuator 12 that is pivotally secured to a base 14 through a pivot connection 16. A piston rod 18 of the actuator 12 is pivotally connected to a bell crank 20 through a pivot connection 22. The bell crank 20 is further pivotally connected to the base 14 through a pivot connection 24. The bell crank 20 provides stroke gain for the loading assembly 2 wherein a connecting rod 27 is pivotally connected to a remote end of the bell crank 20 through a pivot connection 28. If desired, the actuator 12 can be directly coupled to the test specimen 1 without the bell crank 20.

Force feedback is provided to the controller 11 that operates the valve 9. Force feedback can be provided by a load cell 32 that is disposed in the load path of the actuator 12 and the test, specimen 1. In the embodiment illustrated, the load cell 32 is on an end of the connecting rod 27 proximate the test specimen 1. The load cell 32 provides load or force feedback to a controller 40 indicative of axial forces applied to the test specimen 1. The controller 40 receives an output signal from the load cell 32, and based on the desired forced to be applied to the test specimen 1, controls the valve 9 (typically, a servo valve) to displace the piston 8 in the actuator 12 accordingly. Controller 40 operates with direct feedback from the load cell 32. If desired, an accelerometer, not shown, can be incorporated into the load cell 32. The accelerometer can provide an anticipatory drive to the servo valve 9 to help compensate for motion of the test specimen 1 (disturbances to the load control loop). In another embodiment, force feedback can be provided by pressure sensors 33 that measure corresponding pressures in the bore 5 on each side of the piston 8 to determine the amount of force applied.

In the embodiment illustrated in FIGS. 1 and 2, the volume of compressible fluid 3 and container 4 comprise an accumulator (hereinafter indicated by reference numeral 4), wherein at least one accumulator is fluidly coupled to each of the chambers forming the double-acting actuator 12. In this embodiment, two servo valves are indicated at 9 and four accumulators are provided. As stated above, the volume of compressible fluid 3 (herein the accumulators 4) introduce a spring effect to an otherwise substantially rigid actuator. Each accumulator 4 includes a first portion 45 of compressible fluid (typically, a gas such as nitrogen) and a second portion 47 that is filled with a liquid, which compared to the gas, is substantially incompressible. The second portion 47 of each accumulator is fluidly coupled to the bore 5. Commonly, a diaphragm 49 (or equivalent separating device such as a piston) is provided in each accumulator 4 to maintain separation of the gas and the liquid.

Generally, the actuator 12 and the accumulators operate by increasing the compliance of the oil column by several orders of magnitude to allow the servo valve 9 to operate in a maximum-bandwidth load control servo mode into a test specimen 1 of unknown input impedance despite the need for moving load cell control. This technique makes the dominating compliance, which establishes the allowable control loop gain from the oil column be the effective control variable. In the preferred embodiment, with a minimum friction actuator 12 and with a minimum-mass-piston rod and linkage (bell crank 20 and connecting rod 27), the controlled load generated at the piston 8 will also be the load at the load cell 32 despite external disturbing velocities. Even if there is no servo valve action, the spring rate and mass of the attachment point to the test specimen 1 is orders of magnitude lower than would be expected by a conventional load control actuator.

Figure 4:
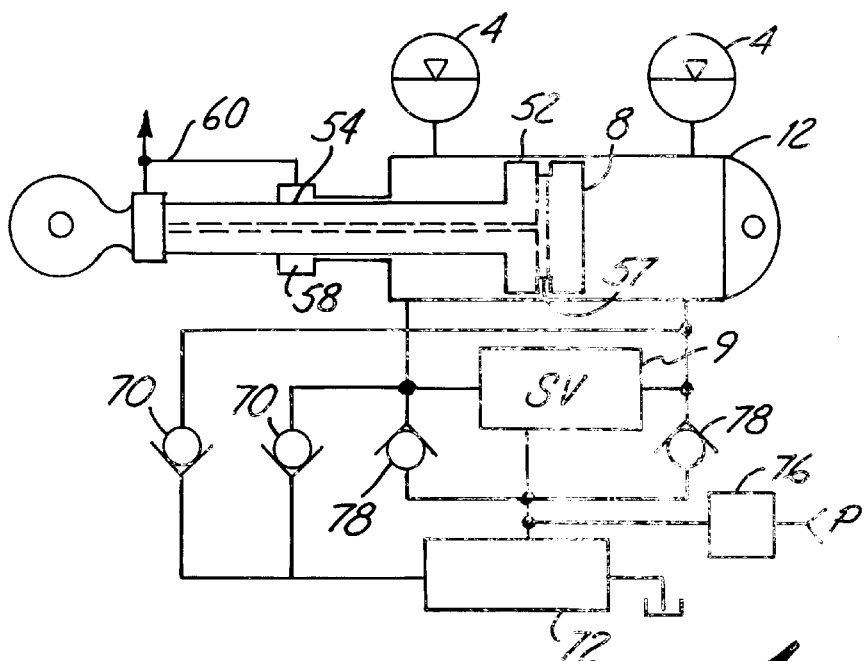
FIG. 4 is a schematic diagram of a control system.

Referring also to FIG. 4, to provide a minimum friction actuator 12, hydrostatic bearings 52 and 54 are provided on the piston 8 and on an endcap 58, respectively. The piston bearings 52 are vented to drain through grooves 57 and ports on and through the center of the piston 8. This oil is collected with the piston rod drain leakage and a pressure reducing valve drain leakage and brought to a collection point with elastomeric hoses indicated at 60.

As stated above, minimum mass is also desired. In a preferred embodiment, the bell crank 20 is made from a light weight, strong material, such as aluminum, while the connecting rod 27 can be made of carbon fiber. Internal components of the actuator 12, such as the piston 8 and associated piston rod 18 can be made from steel. The resulting assembly provides a low inertia assembly.

By use of the volume of compressible fluid 3, the spring component is present within the actuator 12, rather than being connected externally. The spring component provides several feet of virtual deflection. The actuator 12 has a compliance less than 10,000 lbs/in. In a further preferred embodiment, the actuator 12 has a compliance less than 1,000 lbs/in. In yet a further preferred embodiment, the actuator 12 has a compliance less than 400 lbs/in. It should be noted that each of the accumulators can be replaced by a large closed oil volume being used as a liquid spring such as illustrated in FIG. 3. However, when the accumulators are used, the compliance of the actuator 12 can be easily changed by adjusting the pre-charge pressure therein.

In some applications instability can be experienced at hydraulic startup. In particular, the accumulators are often bottomed out on startup, which makes the control loop gain very high. Adding a pressure reducing valve 72 and a check valve 70 (FIG. 4) into each control port of the valve 9 to deliver priority flow to the control ports whenever the system pressure is low alleviates this problem. In addition, the priority flow provided by the check valve 70 prevents the control port pressures from going excessively low on a dynamic program. The pressure reducing valve 72 brings the control ports up to and maintains a selected minimum pressure. Typically, the pressure reducing valve 72 is set slightly higher than the precharge of the accumulators 4.

Figure 5:
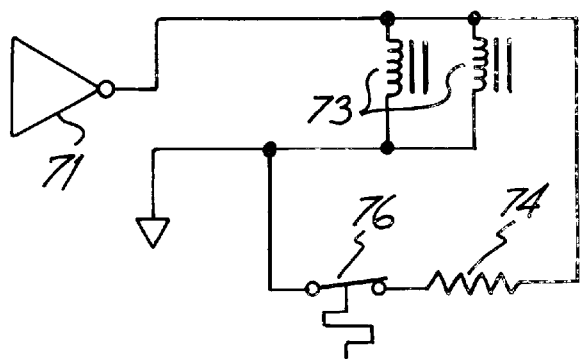
FIG. 5 is a circuit diagram of a servo valve.

Referring to FIG. 5, to further prevent startup instability, some of the control current (indicated at 71) from controller 11 for coils 73 of the servo valve 9 can be shunted through a parallel resistor 74 whenever the main supply pressure is less than a selected threshold. For example, the selected threshold can be ⅔ the normal operating pressure. A pressure switch 76 controls shunting through the resistor 74.

The actuator 12 can generate high temporary uncontrolled forces on hydraulic shutdown due to pressure in the accumulators 4. Referring back to FIG. 4, a dumping path for the control port oil trapped in each operating accumulator can be provided. In the embodiment illustrated, the dumping path is provided by an additional set of check valves 78 from each control port to the system pressure line. Thus, whenever the pressure line is vented, the accumulators 4 are also vented.

In the embodiment of FIG. 3, a spring is provided by compressibility of the hydraulic fluid. As stated above, additional fluid volume provides the spring wherein the additional fluid 3 can be disposed within the bore 5 at either or both ends thereof, or in containers fluidly coupled to the bore 5. Generally, the volume of additional fluid is equal to or greater than the maximum volume of a chamber defined by movement of the piston 8 in the bore 5. In a further preferred embodiment, the volume of additional fluid is at least twice the maximum volume of a chamber defined by movement of the piston 8 in the bore 5. In another preferred embodiment, the volume of additional fluid is at least five times the maximum volume of a chamber defined by movement of the piston 8 in the bore 5. In yet another preferred embodiment, the volume of additional fluid is at least ten times the maximum volume of a chamber defined by movement of the piston 8 in the bore 5. A liquid spring such as provided in FIG. 3 may be preferred in some applications, because a liquid spring is generally more linear than the gas spring of FIG. 2. In addition, the spring rate of a liquid spring is generally more constant with varying cylinder port pressures.

Figure 6:
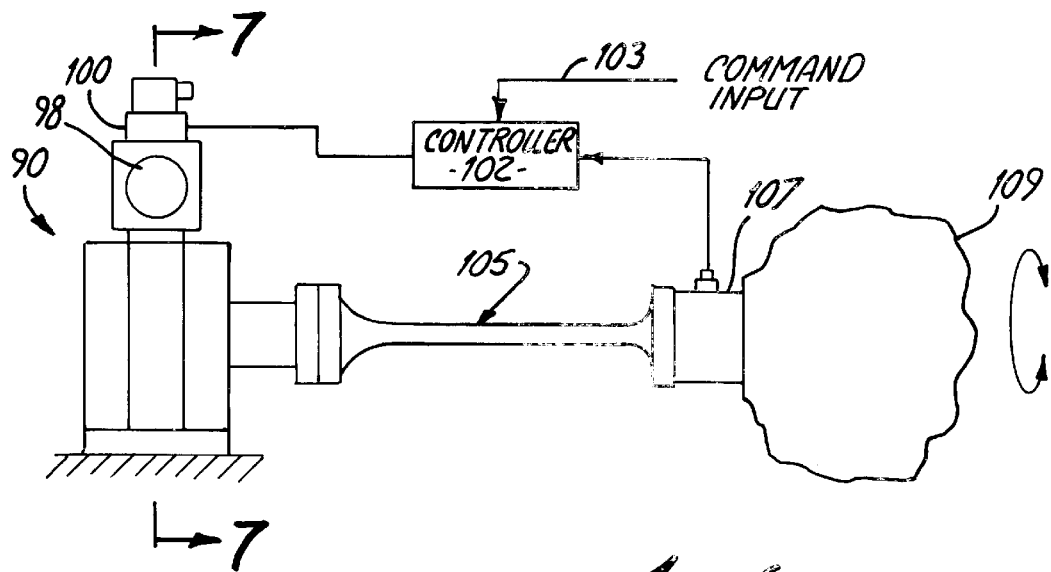
FIG. 6 is a schematic diagram of a third embodiment of the loading assembly.
Figure 7:
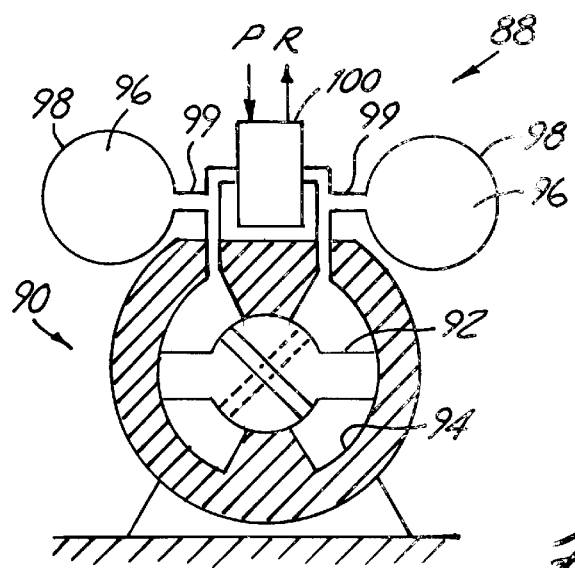
FIG. 7 is a sectional view of the loading assembly of FIG. 6 taken along lines 7—7.

FIGS. 6 and 7 schematically illustrate a loading assembly 88 comprising a rotary actuator 90. Like the linear actuator 12 described above, the rotary actuator 90 operates hydraulically and includes a piston or vane 92 movable in a chamber or bore 94 of a cylinder 97. In the embodiment illustrated, a volume of compressible fluid 96 is disposed within a container 98 that is fluidly coupled to the bore 94 through a short port 99. However, as appreciated by those skilled in the art, the volume of compressible fluid 96 can be disposed within the rotary actuator 90 in the bore 94 on an end thereof, which the piston or vane 92 does not reach.

The piston 92 is slidable in the bore 94 and is operably coupleable to a test specimen, not shown. A valve 100 fluidly coupled to the bore 94 selectively provides fluid to the bore 94 to displace the piston 92. A controller 102 receives a command input 103 and controls the valve 100 to cause nonresonant displacement of the piston 92 in the bore 94. Feedback can be provided by a load cell 107. The rotary actuator 90 can apply significant forces or moments to a test specimen 105, but is also compliant to input velocity or displacement disturbances of the test specimen 105 wherein the volume of compressible fluid 96 acts as a spring. Input disturbances are illustrated schematically at 109 in FIG. 6. Preferably, a minimum mass (i.e., low inertia) piston 92 and output shaft 111 are used.

As with the linear actuators described above, the volume of compressible fluid 96 can comprise an accumulator having a diaphragm or piston separating the volume of compressible fluid 96 such as a gas from a comparably less compressible fluid such as hydraulic oil. Yet in an alternative embodiment, the volume of compressible fluid can comprise excess hydraulic fluid within the bore 94 or a fluidly coupled container 98, as shown. Generally, the volume of additional fluid is equal to or greater than the maximum volume of a chamber defined by movement of the piston 92 in the bore 94. In further embodiments, the volume of additional fluid is twice, five times or ten times the maximum volume of a chamber defined by movement of the piston 92 in the bore 94.

Although the present invention has been described with reference to preferred embodiments, workers skilled in the art will recognize that changes may be made in form and detail without departing from the spirit and scope of the invention. In addition, although illustrated wherein one loading assembly is used, it should be understood that a plurality of loading assemblies can be used in a test system. For instance, a plurality of loading assemblies can be used for active vehicle centering on a test system that supports and provides loads to each spindle of a test vehicle.

What is claimed is:

1. A loading assembly for applying a load to a test specimen, the loading assembly comprising:
    an accumulator having a volume of compressible fluid and a diaphragm separating a chamber from the volume of compressible fluid;
    only a single cylinder/piston actuator for developing a load, the actuator having a cylinder with a bore filled with substantially incompressible fluid and a port opening to the bore, the port being fluidly connected to the chamber of the accumulator, and a piston slidable in the bore and operably coupleable to the test specimen;
    a valve fluidly coupled to the bore to selectively provide incompressible fluid to the bore to displace the piston;
    a second accumulator having a volume of compressible fluid and a diaphragm separating a chamber from the volume of compressible fluid, wherein the chamber is fluidly coupled to a second port opening to the bore on a side of the piston opposite the first-mentioned port, and wherein the valve is fluidly coupled to the bore to selectively displace the piston in opposite directions;
    a controller coupled to the valve to control the valve and cause nonresonant displacement of the piston as a function of a selected load on the test specimen, while tolerating disturbing velocities of the test specimen and the piston; and
    a bell crank pivotally connected to the piston; and a strut pivotally connected to the bell crank at a first end and connectable to the test specimen at a second end.

2. The loading assembly of claim 1 and further comprising a pressure sensing device operably coupled to chambers on opposed sides of the piston to provide a signal indicative of pressures on opposed sides of the piston to the controller.

3. The loading assembly of claim 1 and further comprising a load cell operably coupled in a load path from the piston to the test specimen to measure a load provided to the test specimen and provide a signal indicative of the load to the controller.

4. The loading assembly of claim 1 and pressure regulator fluidly coupled to the bore to maintain a minimum selected pressure on each side of the piston.

5. The loading assembly of claim 4 wherein the pressure regulator includes a first check valve fluidly coupled to the bore on one side of the piston, and a second check valve fluidly coupled to the other side of the piston.

6. The loading assembly of claim 5 and further comprising a third check valve fluidly coupled to the bore on one side of the piston, and a fourth check valve fluidly coupled to the bore on the other side of the piston, the third and fourth check valves adapted to reduce pressure in the bore.

7. The loading assembly of claim 1 wherein the piston and bore comprise a linear actuator.

8. The loading assembly of claim 1 wherein the piston and bore comprise a rotary actuator.

9. A loading assembly for applying a load to a test specimen, the loading assembly comprising:
    a volume of compressible fluid;
    only a single cylinder/piston actuator for developing a load, the actuator having a cylinder with a bore fluidly connected to the volume of compressible fluid, and a piston slidable in the bore and operably coupleable to the test specimen, wherein the volume of compressible fluid is adapted to function as at least equal to a maximum volume of a chamber defined by movement of the piston in the bore;
    a valve fluidly coupled to the bore to selectively provide fluid to the bore to displace the piston;
    a load sensor adapted to provide an output signal indicative of a load applied to the test specimen from the actuator; and
    a controller receiving the output signal and coupled to the valve to control the valve and cause nonresonant displacement of the piston as a function of a selected load on the test specimen, while tolerating distributing velocities of the test specimen and the piston.

10. The loading assembly of claim 9 wherein the volume of compressible fluid is disposed within the bore.

11. The loading assembly of claim 9 wherein the volume of fluid is disposed within a chamber of a container fluidly coupled to the bore through a port.

12. The loading assembly of claim 11 and further comprising:
 a second container having a second chamber filled with a volume of compressible fluid, wherein the second chamber is at least equal to a maximum volume of a chamber defined by movement of the piston in the bore that is fluidly coupled to a second port opening to the bore on a side of the piston opposite the first-mentioned port, and wherein the valve is fluidly coupled to the bore to selectively displace the piston in opposite directions.

13. The loading assembly of claim 12 wherein the first-mentioned chamber of the first-mentioned container is at least five times the maximum volume of the chamber defined by movement of the piston in the bore that is fluidly coupled to the first-mentioned port opening, and wherein the second chamber of the second container is at least twice the maximum volume of the chamber defined by movement of the piston in the bore that is fluidly coupled to the second port opening.

14. The loading assembly of claim 13 wherein the first-mentioned chamber of the first-mentioned container is at least five times the maximum volume of the chamber defined by movement of the piston in the bore that is fluidly coupled to the first-mentioned port opening, and wherein the second chamber of the second container is at least ten times the maximum volume of the chamber defined by movement of the piston in the bore that is fluidly coupled to the second port opening.

15. The loading assembly of claim 14 wherein the first-mentioned chamber of the first-mentioned container is at least ten times the maximum volume of the chamber defined by movement of the piston in the bore that is fluidly coupled to the first-mentioned port opening, and wherein the second chamber of the second container is at least ten times the maximum volume of the chamber defined by movement of the piston in the bore that is fluidly coupled to the second port opening.

16. The loading assembly of claim 9 wherein the volume of compressible fluid is at least twice the maximum volume of the chamber defined by movement of the piston in the bore.

17. The loading assembly of claim 16 wherein the volume of compressible fluid is at least five times the maximum volume of the chamber defined by movement of the piston in the bore.

18. The loading assembly of claim 17 wherein the volume of compressible fluid is at least ten times the maximum volume of the chamber defined by movement of the piston in the bore.

19. The loading assembly of claim 11 wherein the container comprises an accumulator.

20. The loading assembly of claim 9 wherein the load sensor comprises a load cell operably coupled in a load path from the piston to the test specimen.

21. The loading assembly of claim 12 and wherein the load sensor comprises a pressure sensing device operably coupled to chambers on opposed sides of the piston, the output signal being indicative of pressure on opposed sides of the piston to the controller.

* * * * *